United States Patent [19]

Reimels et al.

[11] 4,362,161

[45] Dec. 7, 1982

[54] CRANIAL DRILL

[75] Inventors: Harry G. Reimels, Braintree; Daniel G. Cerundolo, Dedham; Roy W. Downing, Hingham, all of Mass.

[73] Assignee: Codman & Shurtleff, Inc., Randolph, Mass.

[21] Appl. No.: 200,725

[22] Filed: Oct. 27, 1980

[51] Int. Cl.³ ............................................. A61B 17/16
[52] U.S. Cl. ..................................... 128/310; 408/139
[58] Field of Search ................ 128/310, 305.1, 92 E; 408/14, 15, 703, 139

[56] References Cited

U.S. PATENT DOCUMENTS 2,525,669  10/1950  Hainault ............................... 128/310

FOREIGN PATENT DOCUMENTS 1178275  1/1970  United Kingdom ................. 128/310

*Primary Examiner*—Michael H. Thaler
*Attorney, Agent, or Firm*—Donal B. Tobin

[57] ABSTRACT

A completely disposable, permanently assembled drill for perforating bone structures, which includes a generally annular drill body. A primary drill member is slidably and rotatably received in the distal end of the drill body. A driver is slidably and rotatably received in the proximal end of said drill body. A pin and slot-type spring biased clutch is disposed on the confronting surfaces of the drill member and driver. The pin of the clutch projects through the triangular openings and the sidewall of the drill body so as to limit the throw of the clutch and to link the drill body and drill member together. The interaction of the pin against the triangular side of the slot in the drill body produces a component of force which tends to urge the clutch apart. When the drill is placed against the bone structure with a force sufficient to overcome the spring bias, the clutch will engage and the driver and drill member and the drill body will rotate together. The counterbore on the drill body provides a support for the drill mechanism so that the drill member may release when it penetrates the bone structure without having the remainder of the drill move in the direction toward the cranial cavity. The sleeve holds the drill body and driver together and is made of a material that degrades when subjected to sterilization.

13 Claims, 6 Drawing Figures

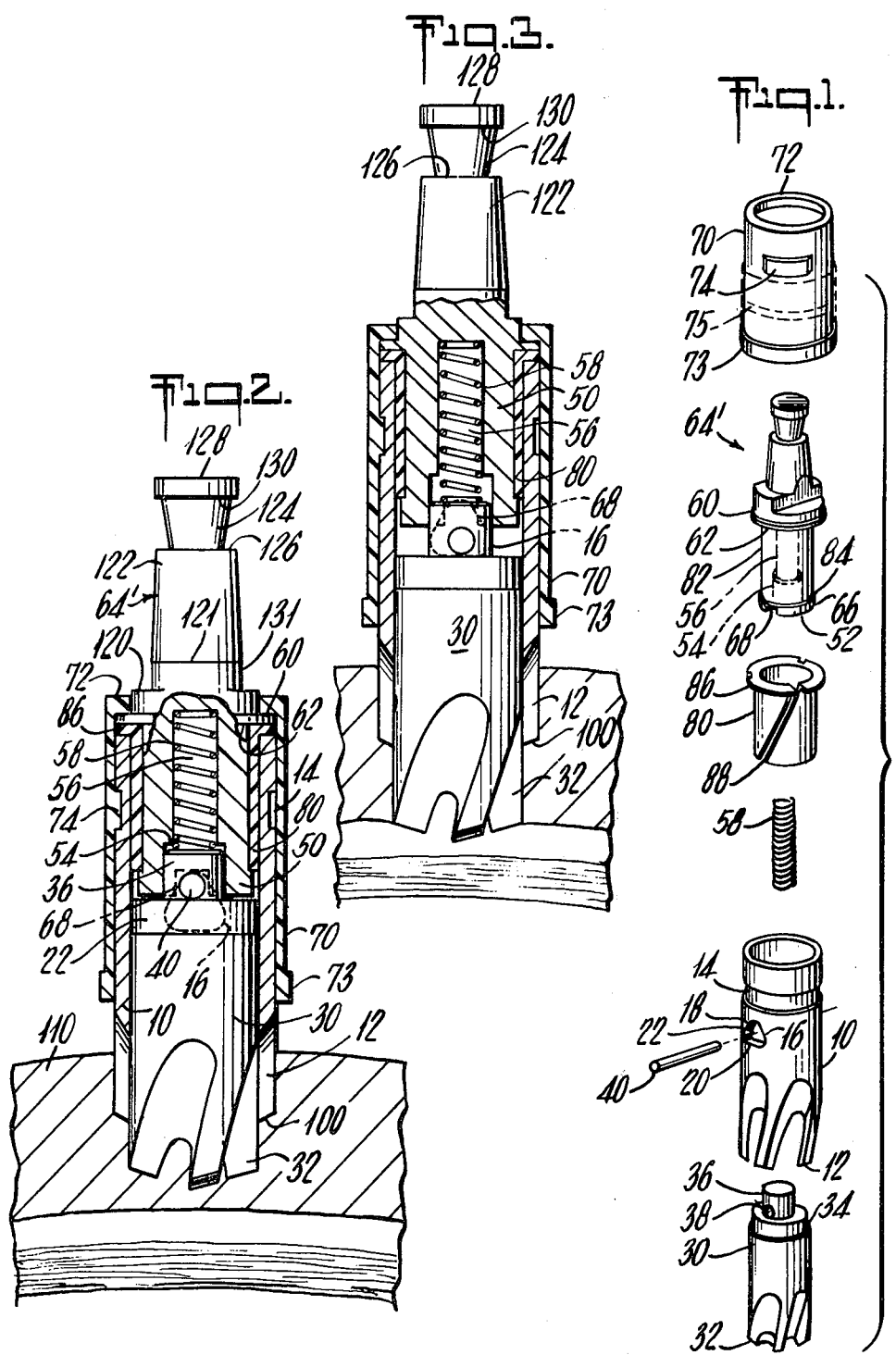

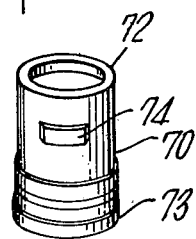
Fig.1A.
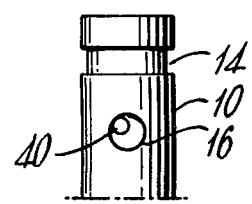
Fig.4.
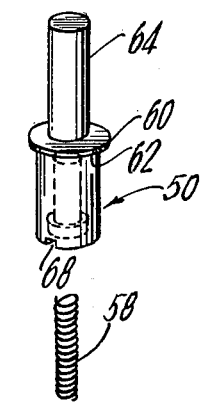
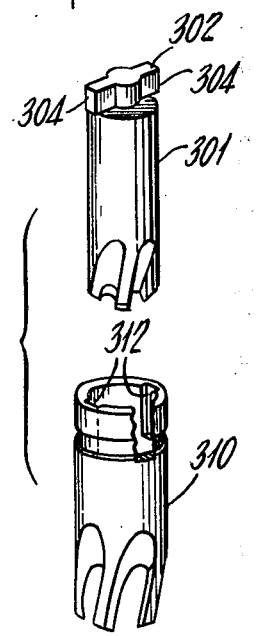
Fig.5.
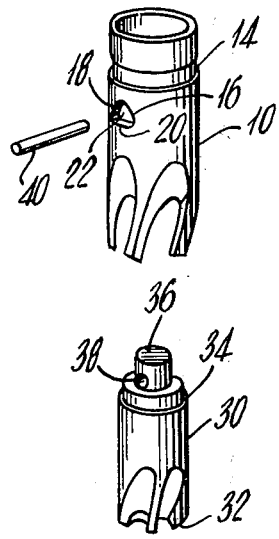

CRANIAL DRILL

FIELD OF THE INVENTION

This invention relates to a medical device, and more particularly to a drill for use by medical practitioners in operations performed on the skull or other bone structure of a human or animal.

BACKGROUND OF THE INVENTION

In many surgical operations it is necessary to obtain direct access to the cranial cavity and the brain. To perform such operations it is often necessary to drill holes through the skull bone. Since the bone is very hard, it is necessary to apply significant pressure to drill through it. Since the dura beneath the skull bone and the brain itself are very delicate, it is important that the drilling cease immediately before the dura is cut or damaged.

In the past, surgeons have used hand braces and bits of a design very similar to those used for non-medical purposes, for example carpentry. Such tools are not completely satisfactory because it has been found that such tools can cut through the skull and damage the meninges or brain and tend not to leave the skull or the underlying membranes in a condition that enables them to heal to approximately their original condition. It has also been found that hand tools are slow and require the surgeon to exert a great deal of energy. Attempts have been made in the past to provide power driven cranial drills which remedied some of these conditions. U.S. Pat. No. 2,842,131, entitled Automatic Drill, by G. W. Smith, discloses a cranial drill. The Smith drill includes a primary drill which is slideable and guidable freely in a tapered safety counterbore collar. The Smith drill includes a clutching mechanism which permits the primary drill to automatically release once the last shelf of the inner table of the skull structure is removed at the base of the opening. The counterbore, made by the counterbore collar, provides a support for the drill mechanism so that the primary drill may release when it penetrates the skull without having the remainder of the drill moved in the direction toward the cranial cavity.

The cutting surfaces of the Smith drill are designed to remove the bone structure in large, generous bone chips so that the chips can be replaced and reincorporated into the whole structure after the operation is performed.

The Smith drill is designed to be dismantled for cleaning and sterilizing. It has been found, however, that the cleaning and sterilizing process can be expensive because skilled personnel must spend significant amounts of time reassembling and testing the drill after cleaning and sterilizing.

Thus, there is a need for a completely disposable, permanently assembled drill, which cannot be dismantled, cleaned, sterilized, reassembled, and periodically sharpened and which includes an indicator to advise the user whether or not attempts have been made to clean or sterilize the drill.

The clutch mechanism in the Smith drill uses a spring force to assist in the disengagement of the drill mechanism from the driver. A cam action provided by the interaction of the component parts of the Smith clutch also provides an axial force on the Smith primary drill to further assist in the disengagement of the clutch as the drill penetrates the bone structure being drilled. It is desirable to have the clutch mechanism disengage as quickly as possible after the primary drill penetrates the skull.

SUMMARY OF THE INVENTION

The present invention provides a completely disposable, low-cost cranial drill which will accomplish both the perforating and burring of the hole with one unit.

Although this drill is particularly well suited for drilling through the skull, it is also useful in perforating bone structures in other parts of the body. This drill assembly is a disposable unit which is assembled and tested in the manufacturer's factory. It is then packaged and sterilized before it is shipped. It is used once and then thrown away. Thus the expense of dissembly, cleaning and sterilizing is eliminated.

The drill of the present invention is designed so that the surgeon will know whether or not the drill has been disassembled or subjected to the more common means of sterilization, i.e., by heat or sterilizing gases like ethylene oxide. The drill is originally assembled with a plastic sleeve which must be mutilated or completely destroyed in order to take the drill apart for cleaning. The plastic will also melt if subjected to sterilizing heat. The drill is also equipped with a label which includes a strip which discolors in the presence of ethylene oxide. Thus, the degradeable sleeve and discoloring label provide information that will allow the surgeon to determine whether the drill has been disassembled or subjected to sterilizing heat or common sterilizing gas.

The drill of the present invention includes a primary drill member with a number of cutting surfaces at its distal end for cutting through a bone structure. A driver, adapted to be connected to a drill, is operatively and selectively connected to the primary drill member through clutch mechanism. In the preferred embodiment a slot and pin-type clutch is used. The proximal end of the primary drill member includes a stem with a radial bore extending therethrough in which a pin may be freely supported. The driver has an axial bore extending into its distal end for accommodating a compression spring, the distal end of which bears against the stem of the primary drill member. This distal end of the driver includes a transverse slot for accepting the pin mounted in the primary drill member. The driver also includes an axial counterbore extending into the distal end of the driver a distance less than the height of the primary drill stem. When the primary drill member and the driver are compressed together against the force of the spring, the pin on the primary drill member will engage the slot on the distal end of the driver so that the two will rotate together. When assembled, the clutch pin bottoms on the clutch slots to keep primary drill member from bottoming in the driver.

The driver and the primary drill member slide into opposite ends of a drill body which includes counterbore cutting flutes on its distal end, a recess circumferentially about the drill body near its proximal end and generally triangular slots through diametrically opposed portions of the drill body wall. Alternatively, the slot may be circular or even oval-shaped. When the driver and primary drill member are assembled inside the drill body, the clutch pin projects into the generally triangular slot to hold the drill body and the primary drill together and to cause the counterbore drill body and the primary drill member to rotate together when the clutch is engaged.

A plastic sleeve, which melts if it is subjected to sterilizing heat and which must be mutilated or completely destroyed to disassemble the drill fits peripherally about the drill body. The sleeve includes a radially outwardly extending protrusion which may be deformed to extend inwardly into the circumferential recess about the drill body to hold the driver and drill body together.

The drill is assembled by inserting the driver, spring, and primary drill member into the drill body and installing the clutch pin. The sleeve is then placed over the drill body and assembled to it by deforming a portion of the sleeve into the drill body recess. The clutch pin projects into the slots and sides of the drill body. The axial length of the slot controls the throw distance of the clutch between the position where the clutch is engaged and where the clutch is disengaged.

The use of a triangular-shaped slot provides a cooperative action between the clutch pin and the sides of the triangle which assist in disengaging the clutch when the primary drill member penetrates the bone structure being drilled.

In the rest position, the spring urges the primary drill member forward until the pin engages the forward portion of the triangular slot in the drill body wall. In this position, the pin which is carried by the primary drill member is disengaged from the slot on the driver so that the clutch is disengaged, and the driver may turn independently of the drill member. When the primary drill is placed against the bone structure with a force sufficient to compress the spring, the primary drill member and the pin which it carries will be urged back toward the driver until the pin bottoms on the slots in the end of the driver at a position near the apex of the triangular slot. At this point, the clutch will be engaged, and the driver and primary drill member will turn together. Also, the drill body, which includes counterbore flutes at its distal end, will be linked together with the primary drill member so that they will rotate as a unit. The pin engages the sidewall of the triangular slot and produces a component of force in the axial direction. When the primary drill perforates the bone structure, this force component will combine with the axial spring force to assist the clutch in disengaging. When the clutch is disengaged, both the primary drill member and the counterbore flutes on the end of the drill body will stop turning.

While the drill is engaged, the primary drill member cutting surfaces project a counterbore distance beyond the end of the counterbore flutes on the drill body. This counterbore forms a shelf which provides support for the drill mechanism so that the primary drill member may release when it penetrates the skull without having the remainder of the drill mechanism move in the direction toward the cranial cavity.

In an alternative embodiment, the driver may include an annular bearing which fits about the central portion of the driver and cooperates with the interior surface of the drill body to provide a suitable bearing.

The driver, primary drill member, clutch pin, spring, and drill body are preferably made of stainless steel. The plastic sleeve is made of a material which will melt when subjected to sterilizing heat and which will break if it is removed to disassemble the drill, so that the user will know whether or not attempts have been made to sterilize or disassemble the drill after it has left the factory environment.

It can be seen that the present invention provides a completely disposable drill useful in perforating bone structures.

BRIEF DESCRIPTION OF THE DRAWINGS

These and other advantages and features of the present invention will become apparent from the following description of certain embodiments of the invention taken in conjunction with the following drawings in which:

FIG. 1 shows an exploded, perspective view of cranial drill of the present invention;

FIG. 1A shows an exploded perspective view of an alternative embodiment of the present invention;

FIG. 2 shows a sectional elevation of the cranial drill of the present invention with the clutch engaged;

FIG. 3 shows a sectional elevation of the cranial drill of the present invention with the clutch disengaged;

FIG. 4 shows an elevational view of a portion of a modified embodiment of part of the drill; and, FIG. 5 shows a sectional perspective of a further modification of the drill.

DETAILED DESCRIPTION OF THE PREFERRED EMBODIMENT

Referring now to FIG. 1, there is shown the drill assembly of the present invention, which includes a generally cylindrical drill body 10 having counterbore flutes 12 extending from the distal end, a recess 14 extending circumferentially about the drill body close to the proximal end and generally triangular shaped slot 16 extending through diametrically opposed portions of the wall of the drill body 10. Generally cylindrical primary drill member 30 fits within the distal end of drill body 10 in a clearance fit so that it may rotate and slide in the axial direction freely. Drill member 30 includes a stem 36 with a transverse bore 38 therethrough.

A generally cylindrical driver 50 fits into the other end of drill body 10. The distal end 52 of drill body 50 includes an axial bore 54 and a coaxial pilot bore 56. Transverse slots 68 extend across distal end 52 of driver 50. Pilot bore 56 houses spring 58.

Driver 50 includes a chuck stem 64, which is adapted to engage the chuck of a drill. The first stem 64, shown in FIG. 1A, is a generally cylindrical, coaxially aligned stem extending from the proximal end of driver 50. This is known as a Jacobs stem. The second stem 64' is shown in FIG. 1 and will be explained in greater detail in connection with FIGS. 2 and 3 and is known as a Hudson stem. Either stem may be used.

A flange 60 extends radially outwardly from driver 50 and provides a bearing surface 62, which is adapted to bear against the confronting surface of the proximal end of drill body 10 when driver 50 is assembled into drill body 10. When primary drill member 30 and driver 50 are assembled into drill body 10, pin 40 extends into slot 16 and stem bore 38 to hold drill member 30 within drill body 10. Transverse slots 68, on distal end 52 of driver 50, are cooperatively disposed to engage pin 40 to form a clutch providing a positive drive for drill member 30. Since pin 40 is long enough to extend into slot 16, it provides a positive drive for drill body 10 and counterbore flutes 12.

Sleeve 70 fits about the periphery of drill body 10 and includes a flange 72 extending radially inwardly and circumferentially about the proximal end of sleeve 70 to provide a means for holding driver 50 in drill body 10. A raised portion 74, extending from the side of sleeve 70, may be deformed into recess 14 of drill body 10 when the driver 50 is assembled completely into drill body 10. An outwardly extending flange 73 extends circumferentially about the distal end of sleeve 70 to act as a stop for the forward motion of drill 10.

As shown in FIG. 1, driver 50 may be fitted with an annular bearing sleeve 80 having a flange 86 extending radially outwardly and circumferentially about bearing 80. Bearing 80 includes a spiral slot 88 extending along its entire length. Driver 50 accommodates bearing 80 by including a recess 82 along its central portion from driver flange bearing surface 62 almost to the distal end of driver 50. Bearing 80 is made of a resilient material which has a relaxed outer diameter somewhat greater than the interior diameter of drill body 10. When bearing 80 is installed in recess 82 on driver 50 and then driver 50 is inserted into drill body 10, resilient bearing 80 is slightly compressed so that the resilient force keeps it in intimate frictional contact with the interior surface of drill body 10 permitting driver 50 to rotate freely.

In an alternative embodiment shown in FIG. 1A, bearing 80, recess 82 and lip 84 may be omitted so that driver 50 fits directly into drill body 10 and is freely rotatable and slidable therein.

Referring again to FIG. 1, the individual parts of the drill of the present invention will be described in greater detail. An annular drill body 10 includes counterbore cutting flutes 12 at its distal end and a recess 14 circumferentially about drill body 10 near its proximal end. Slots 16 extend through diametrically opposed portions of the sidewall of annular drill body 10. The peripheral surface 18 of slot 16 defines a generally triangular cam surface where the base 20 of the triangle is aligned generally circumferentially of drill body 10 and the sides 22 of the triangle are aligned at an angle to axis of drill body 10.

Generally cylindrical primary drill member 30 is received in the distal end of drill body 10 with a clearance fit so that it is freely rotatable within drill body 10 and slideable in the axial direction within drill body 10. Drill member 30 includes cutting surfaces 32 at its distal end, preferably four in number, and a slightly recessed circumferential lip 34 about its distal end.

Drill member 30 includes a coaxially aligned, generally cylindrical stem 36 extending from its proximal end into drill body 10. Stem 36 has a transverse bore 38 drilled through it for accepting pin 40. When the drill assembly is assembled, drill member 30 is inserted into drill body 10 far enough so that bore 38 lines up with slot 16 in the wall of drill body 10. Pin 40 is inserted through slot 16 on one side of drill body 10 through drill member bore 38 and into slot 16 on the other side of drill body 10. The length of pin 40 is shorter than the outside diameter of drill body 10 and longer than the inside diameter of drill body 10 so that the edges of pin 40 may engage the circumferential surface 18 of slot 16 and limit the axial travel of drill member 30 within drill body 10 and couple drill body 10 and drill member 30 to rotate together.

Pin 40 fits loosely into stem bore 38 so that despite slight variances in manufacturing tolerances of the assembled parts of the drill, the clutch will still work well. For example, a loosely fitting pin provides automatic self-correcting alignment if the slot 16 or stem bore 38 are slightly off center. This permits the drill parts to be interchangeable. Thus, each part does not require hand machining or finishing in order to permit the mechanism to work correctly.

A generally cylindrical driver 50 is inserted into the proximal end of drill body 10 and will freely rotate and slide in the axial direction in drill body 10. The distal end 52 of each driver 50 (FIGS. 1 and 1A) includes an axial bore 54 extending coaxially into driver 50 a distance less than the axial height of drill member stem 36. Pilot bore 56 extends into driver 50 from the floor of axial bore 54 a distance sufficient to accommodate a compression spring 58. Surrounding axial bore 54, at the distal end of driver 50, is an annular flange 66. Slots 68 are provided on diametrically opposed sides of annular flange 66. The depth of slots 68 is preferably slightly less than the diameter of pin 40.

A flange 60 extends radially outwardly from and circumferentially about the proximal end of driver 50 and includes a bearing surface 62 facing the opposed surface of drill body 10. The outer diameter of flange 60 is approximately equal to the outer diameter of drill body 10. Driver 50 includes a coaxial stem 64 extending from the proximal end of driver 50, which stem is adapted to be received into the chuck of the drill. The principal difference between the two drivers 50 shown in FIGS. 1 and 1A are the types of chuck stems that are used on the driver. The different chuck stems will be discussed in greater detail subsequently in the application.

Generally cylindrical sleeve 70, fits with a loose clearance fit, about the outside of drill body 10. Inwardly projecting radial flange 72 extends circumferentially about the proximal end of sleeve 70. Flange 72 interferes with the proximal end of flange 60 of driver 50 so that when sleeve 70 is pushed onto drill body 10, flange 72 holds driver 50 in position within drill body 10. Sleeve 70 is long enough so that when driver 50 is held in position with bearing surface 62 against the confronting bearing surface of drill body 10, sleeve 70 covers slot 16 so that pin 40 will not fall out of bore 38. Sleeve 70 includes a raised portion 74 extending circumferentially on sleeve 70, partially thereabout, and is axially aligned with recess 14 on drill body 10. Raised portion 74 may be deformed radially inwardly to engage recess 14 on drill body 10 to hold sleeve 70 and driver 50 on drill body 10. Sleeve 70 also includes an outwardly extending flange 73 extending circumferentially about its distal end to provide a stop for the forward motion of the drill.

Sleeve 70 is made of a plastic material which will melt when subjected to sterilizing heat and which will be mutilated or destroyed if removed to disassemble the drill. Sleeve 70 is equipped with an adhesive label 71 which includes a chemically treated strip 75 which will discolor when subjected to a common sterilizing gas like ethylene oxide. Thus, the user will be able to determine whether the drill has been disassembled or subjected to sterilizing heat or gas.

The plastic material provides good bearing surfaces between the proximal end of driver flange 60 and the inside of the sleeve of flange 72 so that the two parts may rotate with respect to one another. The inside surface of sleeve 70 is also a good bearing surface so that the deformed interior surface of raised portion 74 may slide freely in recess 14. Thus, although sleeve 70 holds driver 50 and drill body 10 together, it freely rotates with respect to both parts so that it will not tend to bind the drill assembly.

The operation of the invention will now be described in conjunction with FIG. 1A. The outer diameter of driver 50 is chosen to provide a clearance fit between driver 50 and drill body 10 when driver 50 is inserted within drill body 10 so that driver 50 will freely rotate and slide axially within drill body 10. When driver 50 is inserted into the proximal end of drill body 10 with spring 58 positioned in pilot bore 56 and extending slightly beyond the distal end of driver 50, the distal end of spring 58 will bear against the proximal surface of drill member stem 36, and slots 68 will be aligned with pin 40 so that when driver 50 is completely inserted into drill body 10 so that bearing surface 62 bears against the confronting proximal end surface of drill body 10, slots 68 and pin 40 will be aligned to form a clutch. When the drill assembly is pushed against the bone structure to be drilled with sufficient force to move drill member 30 into drill body 10 against the force of spring 58, pin 40 will slide into slots 68 and provide a positive drive for drill 30 and drill body 10. The spring force of spring 58 is chosen so that it may be comfortably overcome by the surgeon to engage the clutch. With the clutch engaged, the drill member and driver are coupled together to rotate as a unit and cut through the bone structure. Pin 40 interacts with the sidewalls of peripheral surface 18 of slot 16 so that drill body 10 is also caused to rotate as a unit together with drill member 30 and driver 50. Thus the drilling assembly will bore and counterbore at the same time.

Once drill member 30 penetrates the bone structure, the combined force of spring 58 and the axial force of slot 16 on pin 40 will force drill member 30 forward, carrying pin 40 out of engagement with slots 68 so that drill member 30 and correspondingly drill body 10 will stop rotating almost immediately.

It will be appreciated that the interaction of pin 40 with the sidewall 22 of peripheral surface 18 of slot 16 produces an axial force component which tends to urge drill member 30 forward. This force component will accelerate the decoupling of the clutch mechanism by assisting pin 40 from disengaging slots 68 on driver 50.

The combined force of spring 58 and the axial force of slot 16 on pin 40 provides sufficient forward bias to drill member 30 to force drill member 30 forward just before it drills completely through the bone. As the remaining bone becomes thinner and thinner, it will begin to bend under the bias force provided on the drill body. As the remaining bone becomes very thin, the bias force will move drill member 30 and the remaining bone forward and disengage the clutch before the drill goes completely through the bone.

To further facilitate this clutch disengagement, the edges of slot 68 may be slightly rounded or the sidewalls of slot 68 may be slightly tapered so that the distal end of each end is opened wider than the base of each slot. Alternatively, slot 16 need not be triangular but may be axially aligned.

In a further alternative, the slot may be circular as shown in FIG. 4, or even oval. For the circular embodiment, pin 40 interacts with the wall of the circular slot in much the same fashion as the embodiment of FIG. 1.

As shown in FIG. 5, a different kind of clutch may be employed. A modified drill member 301 includes a stem 302 with ears 304 extending from stem 302 a short radial distance beyond the outer periphery of drill member 301. Modified drill body 310 includes axially aligned, diametrically opposed slots 312 into which ears 304 slide when drill member 301 is assembled into drill body 310. Ears 304 engage slots 68 on a driver 64 like that discussed with the embodiment of FIG. 1. Slots 312 may be inclined to the axis of body 310, and the edges of ears 304 may be rounded so that the interaction of ears 304 and slots 312 will provide an axial force component to assist in disengagement of the clutch.

In the embodiment of FIG. 1, a flanged annular bearing 80 may be used as a bearing between driver 50 and the interior of drill body 10. In this embodiment, the central portion of driver 50 includes a circumferential recess 82 extending thereabout from driver flange 60 almost to the distal end of driver 50. A raised lip 84 is left between the distal end of recess 82 and the distal end of driver 50. Bearing 80 has a radially extending flange 86 extending circumferentially about its proximal end and it has an outer diameter substantially equal to the outer diameter of driver flange 60. Flange 86 is placed between bearing surface 62 of driver flange 60 and the opposed bearing surface of the proximal end of drill body 10 to facilitate smooth rotation of driver 50 with respect to drill body 10. Bearing 80 has a spiral slot 88 extending from its proximal to its distal end. Bearing 80 is made of a resilient material which is resilient in the radially outward direction and has a relaxed outer diameter slightly greater than the inner diameter of drill body 10. The relaxed inner diameter of bearing 80 is slightly greater than the outer diameter of the recessed portion 82 of driver 50. Bearing 80 fits into recess 82 on driver 50 and is held against axial movement by the engagement of the distal end of bearing 80 against lip 84 and by engagement of flange 86 against bearing surface 62. In the relaxed position, bearing 80 has a loose clearance fit in recess 82. When the assembled driver 50 and bearing 80 are inserted into drill body 10, bearing 80 is slightly radially compressed so that it has intimate frictional contact with the inside surface of drill body 10 so that during operation bearing 80 tends to remain stationary with respect to drill body 10 and to permit driver 50 to rotate freely within bearing 80 to provide a smooth bearing surface. With this embodiment of the invention, the dimensions of the thickness of flange 60 and diameter of recess 82 are chosen to account for the additional thickness of liner flange 86 so that all of these parts fit together well without binding or undesired interference.

Referring now to FIG. 2, there is shown an elevational view of the drill assembly of the present invention shown partially in section to reveal the internal workings of the drill assembly. FIG. 2 shows drill member 30 extending partially into skull 110 and with the front faces 100 of flutes 12 of the counterbore also extending into the skull so that flutes 12 rest upon the shoulder provided by the counterbore. The clutch mechanism can be observed. Pin 40 is inserted through triangular slot 16 in drill body 10 and through drill member stem bore 38 and through slot 16 on the other side of drill body 10 (not shown). The base of slots 68 engages the circumference of pin 40, but the proximal surface of stem 36 does not bottom on axial bore 54 of driver 50. Correspondingly, the distal end of driver 50 does not bottom on the confronting proximal end of drill member 30. Stem 36, bore 38, slots 68 and pin 40 form a pin-slot type clutch mechanism to provide a positive drive for drill member 30 when the clutch is engaged. In the preferred embodiment, pin 40 is supported in bore 38 on drill member stem 36, and cooperating slots 68 are disposed on driver 50. Axial bore 54 and pilot bore 56 are also disposed on driver 50. In FIG. 2, it can also be observed that pin member 40 engages sidewall 22 of peripheral wall 18 of slot 16 just short of the vertex of the triangular shaped slot 16. Since pin 40 extends into slot 16, it will carry drill body 10 with it when the clutch is engaged so that drill body 10 and counterbore flutes 12 will rotate together with drill member 30. The side 22 of triangular peripheral surface 18 forms a cam surface with pin 40 and produces an axial force component which tends to urge drill member 30 away from driver 50 so as to tend to disengage the clutch. Thus it can be seen that when the cutting surfaces of drill member 30 penetrate the bone, and just before the clutch mechanism disengages, the axial force component will tend to disengage the clutch. This force, together with the spring force provided by compressing spring 58, will disengage the clutch mechanism and free drill member 30 and drill body 10 from the direct drive of driver 50 as soon as the cutting edges at the distal end of drill member 30 penetrate the bone structure.

As previously explained, the combined spring force of spring 58 and the axial force from the interaction of pin 40 on slot 16 provides a sufficient bias to urge drill member 30 forward just before it drills completely through the bone. As the remaining bone becomes thinner, it will begin to bend under this bias force so that the clutch will disengage before the drill goes completely through the bone. This residual piece of remaining bone may then be carefully removed by the surgeon by hand.

Although the axial force from the interaction between pin 40 and slot 16 is sufficient by itself to disengage the clutch when the drill penetrates the bone, it has been found preferable to include spring 58. Spring 58 keeps the clutch disengaged while the drill is not operating so that the surgeon must push the drill against the surface to be drilled with a positive and noticeable force. This provides positive assurance to the surgeon of the position of the clutch and adds a safety feature. Thus, the clutch cannot engage prematurely and can only engage when the surgeon takes a positive step to engage it.

Also referring to FIG. 2, the placement of bearing 80 can be clearly observed in recess 82 of driver 50 between driver flange 60 and flange bearing surface 62.

Radially extending flange 86 provides a bearing between driver bearing surface 62 and the confronting proximal end surface of drill body 10 to facilitate free rotation of driver 50 with respect to drill body 10 when the clutch is disengaged.

Still referring to FIG. 2, one can clearly see the interrelation of sleeve 70 with the exterior surface of drill body 10. Proximal flange 72 rests against the proximal surface of driver flange 60. As sleeve 70 is pushed forward so that raised portion 74 aligns with recess 14 on drill body 10, spring 58 will compress against the confronting surface of drill member stem 36. Raised portion 74 may then be deformed into recess 14 so that driver 50 is held in proper position. Raised portion 74 may be deformed mechanically or by ultrasonic welding or by other suitable means. Raised member 74 in this preferred embodiment extends only partially around the circumference of recess 14. However, it is possible that raised portion 74 may extend completely circumferentially around recess 14.

Referring now to FIG. 3, there is shown the drill assembly of the present invention with the clutch disengaged. Once the drill member 30 has penetrated the bone structure, the spring 58 and the axial force from the interaction of pin 40 and slot 16 will urge stem 36 forward so that pin 40 disengages slots 68. Driver 50 may continue to spin, but with the clutch disengaged, both drill member 30 and drill body 10 will stop rotating.

The alternative chuck stem 64' is shown particularly in FIGS. 2 and 3. This chuck stem is known as a Hudson stem. A generally cylindrical base 120 extends from driver flange 60 and has a diameter slightly less than the diameter of driver flange 60. A generally conical stem 122 extends coaxially from base 120 and tapers radially inwardly in a direction toward the proximal end of driver 50. At the point where base 120 and stem 122 meet, a shelf 121 is formed. A reverse conic section 124 extends coaxially from stem 122 and tapers radially outwardly in a direction toward the proximal end of driver 50. At the point where stem 122 and reverse conic stem 124 meet a shelf 126 is formed.

Reverse conic stem 124 terminates in a generally cylindrical section 128. The point where cylindrical section 128 and reverse conic section 124 meet provides a shelf 130. Diametrically opposed portions of base 120 are milled away so that shelf 121 forms a key to be received into the drill chuck. A flat spot 131 is left on stem 122.

It can be seen from FIG. 2 that the axial force exerted by the user in drilling the bone structure is transmitted through driver 50 to both primary drive member 30 and counterbore drill body 10. Part of the axial force exerted on driver 50 is transmitted through driver flange 60 and bearing flange 86 to drill body 10. The remainder of the axial force exerted on driver 50 is transmitted through pin 40 to primary drill member 30. Thus while the drill is cutting through the bone structure, sufficient force is transmitted to counterbore flutes 12 of body 10 and primary cutting surfaces 32 of primary drill member 30. When primary drill member 30 penetrates the bone structure, the entire axial force exerted on the drill will be transmitted to the forward faces 100 of counterbore flutes 12. Flutes 12 rest against the bottom of the counterbore hole and support the drill mechanism so that when the primary drill releases when it penetrates the skull, the remainder of the drill will not move forward toward the cranial cavity.

While the present invention has been described in connection with certain preferred embodiments, those skilled in the art will appreciate that certain modifications may be made without departing from the scope of the present invention. It is, therefore, not intended that the present invention be limited except as set forth in the following claims.

We claim:

1. An apparatus for drilling bone structure comprising:
   a generally cylindrical primary drill member having cutting surfaces at the distal end thereof and having a proximal end;
   a generally cylindrical driver having a distal end disposed in confronting relationship with said drill member proximal end and having a proximal end;
   a stem projecting from the proximal end of said driver and adapted for insertion into a drill chuck;
   a clutch means including:
   a cylindrical stem projecting axially from the proximal end of the primary drill member and having a diameter less than the diameter of the primary drill member, said stem including a bore extending generally radially completely therethrough;
   said driver including an axial bore extending into the distal end thereof a distance less than the height of said drill member stem and adapted to receive said drill member stem with a clearance fit, said bore leaving an annular flange surrounding the distal end of said driver;

a slot extending radially completely across said annular flange in communication with said axial bore;

a pin extending completely through said drill member stem and engaging the driver transverse slot on both sides of said drill member stem;

a generally annular drill body slidably and rotatably receiving said drill member and said driver, said drill body wall having diametrically opposed openings extending therethrough and wherein the periphery of said openings in said drill body wall forms a cam surface having a generally triangular shape, with the base of said triangular cam surface aligned along the circumference of said drill body, and wherein the sides of said triangular cam surface are aligned at an angle to the axis of the drill body;

said pin extending from said drill member stem bore into said triangular openings and adapted to engage the peripheral cam surfaces thereof;

the axial height of said triangular cam limiting the throw distance of said clutch;

the interaction of said pin with the sides of the triangular shaped cam surface providing a means for directing a component of the force between the cam surface and the pin along the axis of the primary drill to urge said drill member away from said driver to accelerate the decoupling of said drill member from said driver to more quickly disengage said clutch means and thereby decrease the possibility of said drill member injuring tissue or organs disposed about the inside of the bone structure;

said clutch means further including a coaxial pilot bore extending into said driver from the distal end thereof and having a diameter less than the diameter of said drill member stem;

a compression spring bottomed on said pilot hole and bearing against said drill member stem for urging said driver and said drill member apart so as to provide a resistance force to the engagement of said clutch means which may be overcome when the drill member is placed against the bone structure and drilling begins;

said compression spring assisting and decoupling said clutch means when said drill member drills through the bone structure.

2. The apparatus of claim 1 wherein the depth of said driver transverse slot and the location of said drill member stem bore cooperate so that when said pin is in position in the stem bore and engaged in the driver slot, the proximal end of the drilling member stem does not bottom in said driver axial bore, and the distal end surface of the driver does not bottom on the confronting surface of the drill member.

3. The apparatus of claim 1 wherein said drill body includes counterbore cutting edges extending from the distal end thereof a sufficient distance to permit the cutting edges of said primary drill member to extend axially beyond the distal end of said counterbore cutting edges a distance equal to the desired counterbore when said drill member and said driver are coupled together through said clutching means.

4. The apparatus of claim 1 further including an annular sleeve disposed about said drill body and covering said opening in said drill body wall and including a flange at its proximal end extending radially inward to interfere with the radially extending flange on said driver;

a recess extending at least partially about the exterior surface of said drill body and adapted to receive a deformable portion of said sleeve for holding said driver and said drill body together so that they will not separate in the axial direction.

5. The apparatus of claim 4 wherein said sleeve is made of a degradeable material that degrades if subjected to sterilizing heat.

6. The apparatus of claim 4 wherein said sleeve is made of a material which will break if said sleeve is removed to disassemble said drill apparatus.

7. The apparatus of claim 4 further including means disposed on the exterior of said sleeve for indicating whether the drilling apparatus has been exposed to sterilizing chemicals.

8. The apparatus of claim 1 wherein said pin fits into said stem bore with a clearance fit to thereby provide a self-correction feature if said pin and said slot are slightly off center.

9. The apparatus of claim 1 wherein the proximal end of said drill body includes a bearing surface; and, wherein said driver includes a generally radially extending flange about the proximal end of said driver facing said drill body bearing surface.

10. The apparatus of claim 9 wherein said driver includes a raised circumferential flange extending about the distal end thereof;

a generally annular bearing of a resilient material having a spiral slot extending therealong so that said bearing is resilient in the radial direction; and, having a radially extending flange extending substantially about the circumference of one end of the bearing;

said bearing disposed about said driver between said raised distal flange and said radially extending proximal flange;

whereby when said bearing and said driver are inserted into said drill body, said resilient bearing expands into intimate frictional contact with the interior wall of said drill body and permits said driver to freely rotate therewithin, and said bearing circumferential flange provides a bearing surface between the confronting surfaces of said driver proximal flange and the adjacent bearing surface on the end of said drill body.

11. An apparatus for drilling bone structures comprising:

a generally annular drill body having generally triangular shaped, diametrically opposed openings extending therethrough, the bases of said triangular shaped openings being aligned generally circumferentially about said drill body and the sides of said openings being aligned at an angle to the axis of said drill body, the proximal end of said drill body including a bearing surface;

a generally cylindrical primary drill member freely, slidably and rotationally disposed within said drill body and having cutting surfaces on the distal end thereof;

a generally cylindrical drill driver rotatably and slidably disposed into the proximal end of said drill body and having a stem projecting from the proximal end thereof adaptable for insertion into a drill chuck;

a generally radially extending flange about the proximal end of said driver facing said drill body bearing surface for limiting the extent which said driver extends into said drill body;

a slot and pin-type clutch mechanism cooperatively disposed on the opposing proximal end of said drill member and said distal end of said driver;

the pin of said pin and slot clutch extending through the openings in said drill body wall and interacting with the base of said triangular slot to limit the forward movement of the drill member when the clutch is decoupled and interacting with the side of said triangular opening when the clutch is coupled so that when the drill member penetrates said bone structure, the component of force between the pin and the openings tends to accelerate the coupling of the clutch;

said clutch means further including a compression spring disposed between confronting surfaces of said drill member and said driver for urging the two apart and providing a resistance force which is overcome when the drill member is pushed against the bone structure and drilling begins.

12. The apparatus of claim 11 wherein said drill body includes counterbore cutting edges on the distal end thereof;

the distal cutting edges of said drill member extending, when said clutch is engaged, a counterbore distance beyond the distal end of the counterbore cutting edges;

whereby when said counterbore begins to cut, the drill member is already drilled a distance into the bone structure, the counterbore forming a counterbore shelf to at least partially absorb the pressure of the user pushing the drill forward.

13. The apparatus of claim 11 wherein said drill body includes an annular recess extending circumferentially about the outer surface of said drill body;

an annular sleeve extending about the periphery of said drill body and including a proximal flange extending radially inwardly and interfacing with the proximal flange on said driver;

deformable locking means on said sleeve adapted to be deformed into said drill body recess;

said sleeve compressing said driver flange against said drill body and compressing said spring.

* * * * *